United States Patent [19]

Weigert

[11] Patent Number: 4,734,503

[45] Date of Patent: Mar. 29, 1988

[54] CATALYTIC TRANSHALOGENATION OF HALOAROMATICS

[75] Inventor: Frank J. Weigert, Wilmington, Del.

[73] Assignee: E. I. Du Pont De Nemours and Company, Wilmington, Del.

[21] Appl. No.: 827,011

[22] Filed: Feb. 7, 1986

[51] Int. Cl.$^4$ .................. C07D 211/72; C07C 21/24; C07C 25/13; C07C 17/00

[52] U.S. Cl. .................................. 546/345; 570/144; 570/143; 570/151; 570/147; 570/163; 558/425

[58] Field of Search ............... 546/345; 570/144, 143, 570/151; 558/425

[56] References Cited

U.S. PATENT DOCUMENTS 3,231,625  1/1966  Nyman ............................... 570/144
3,852,365  12/1974 Mahler ............................... 570/144

OTHER PUBLICATIONS

Seko, Maomi; Development of Asahi Chemical Chlor-Alkali Technology, Int. Chlorine Syposium, 1982, pp. 15-28.

Primary Examiner—Henry R. Jiles
Assistant Examiner—Robert C. Whittenbaugh
Attorney, Agent, or Firm—James A. Costello

[57] ABSTRACT

Catalytic transhalogenation of haloaromatics according to the equation:

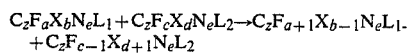

$$C_zF_aX_bN_eL_1 + C_zF_cX_dN_eL_2 \rightarrow C_zF_{a+1}X_{b-1}N_eL_1 + C_zF_{c-1}X_{d+1}N_eL_2$$

wherein:

when $C_z$ is a benzene derivative, $a+b=5$; $e=0$; $c+d=5$; $z=6$;

when $C_z$ is a pyridine derivative, $a+b=4$; $e=1$; $c+d=4$; $z=5$;

when $C_z$ is a naphthalene derivative, $a+b=7$; $e=0$; $c+d=7$; $z=10$; and when $C_z$ is a biphenyl derivative, $a+b=9$; $e=0$; $c+d=9$; $z=12$;

$L_1$ and $L_2$, alike or different, are selected from F, Cl, Br, H, CN, $C_nF_{2n+1}$, and $C_6F_5$;

X is Cl, Br, or I when $C_z$ is a benzene derivative; and n is 1 to 12. This method is a novel route to known haloaromatic compounds.

33 Claims, No Drawings

CATALYTIC TRANSHALOGENATION OF HALOAROMATICS

BACKGROUND OF THE INVENTION

U.S. Pat. No. 3,852,365 discloses the preparation of perchlorofluorobenzenes by heating a reaction mixture consisting essentially of two or more perhalobenzenes selected from the group consisting of hexachlorobenzene, hexafluorobenzene and perchlorofluorobenzenes in which the number of chlorine or fluorine atoms in the components of the mixture differ by at least two. The reaction is conducted in sealed gold tubes at 500° C. for three hours under 500 to 1000 atmospheres of pressure. No catalyst is present other than the interior of the gold tube.

U.S. Pat. No. 3,231,625 discloses the disproportionation of tetrafluorodichlorobenzene and trifluorotrichlorobenzene. The reaction is conducted at temperatures above 600° C. in the presence of an aluminum fluoride catalyst. Below 600° C. little or no disproportionation occurs.

SUMMARY OF THE INVENTION

This invention concerns the catalytic rearrangement of haloaromatic compounds according to the general equation:

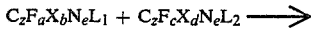

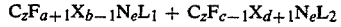

wherein:
when $C_z$ is a benzene derivative, $a+b=5$; $e=0$; $c+d=5$; $z=6$;
when $C_z$ is a pyridine derivative, $a+b=4$; $e=1$; $c+d=4$; $z=5$;
when $C_z$ is a naphthalene derivative, $a+b=7$; $e=0$; $c+d=7$; $z=10$; and
when $C_z$ is a biphenyl derivative, $a+b=9$; $e=0$; $c+d=9$; $z=12$;
$L_1$ and $L_2$, alike or different, are selected from F, Cl, Br, H, CN, $C_nF_{2n+1}$, and $C_6F_5$;
X is Cl, Br, or I when $C_z$ is a benzene derivative; and n is 1 to 12;
in the presence of a catalyst selected from at least one of:
  (i) $Cr_2O_3$ and $Al_2O_3$ alone or together;
  (ii) $Cr_2O_3$ and one or more members from the group MnO, $MnO_2$, $P_2O_5$, $B_2O_3$, $La_2O_3$, ZnO, $Fe_2O_3$, NiO, Pd, $WO_3$, CoO, $V_2O_5$, $CuCl_2$, CuO, PbO, $Bi_2O_3$, FeO, NiO, CoO, $ZrO_2$, $TiO_2$, MgO and $CrCl_3$; and
  (iii) $Al_2O_3$ and one or more members from the group MnO, $MnO_2$, $P_2O_5$, $B_2O_3$, $La_2O_3$, ZnO, $Fe_2O_3$, NiO, Pd, $WO_3$, CoO, $V_2O_5$, $CuCl_2$, CuO, PbO, $Bi_2O_3$, FeO, NiO, CoO, $ZrO_2$, $TiO_2$, MgO, and $CrCl_3$.

When I=II, the reaction is a disproportionation reaction wherein III≠IV. When I≠II, the reaction is a transhalogenation reaction wherein III may or may not be the same as IV and at least one of III or IV will be different from I and from II.

In the foregoing compound formulae when $C_z$ is a benzene derivative, each of a, b, c or d is 0 to 5 so long as $a+b=5$ and $c+d=5$; when $C_z$ is a pyridine derivative, each of a, b, c or d is 0 to 4 so long as $a+b=4$ and $c+d=4$; when $C_z$ is a naphthalene derivative, each of a, b, c or d is 0 to 7 so long as $a+b=7$ and $c+d=7$; and when $C_z$ is a biphenyl derivative, each of a, b, c or d is 0 to 9 so long as $a+b=9$ and $c+d=9$. The most preferred reactants are benzene derivatives, i.e., $z=6$.

When X is defined as "Cl, Br", it is meant that X can be Cl or Br or a combination of Cl and Br consistent with the foregoing definitions for a, b, c and d. When $C_z$ is a benzene derivative and iodine is present, then X can be I, or Cl and I, or Br and I, or Cl, Br and I consistent with the foregoing definitions for a, b, c and d.

DETAILS OF THE INVENTION

Representative aromatic compounds suitable for the process of this invention are:
$C_6F_aX_bL$ ($C_z$ is a benzene derivative) X=Cl, Br, I; $a+b=5$; L=F, Cl, Br, H, CN, $C_nF_{2n+1}$, n=1 to 12, $C_6F_5$.
$C_5F_aX_bNL$ ($C_z$ is a pyridine derivative) X=Cl, Br; $a+b=4$; L=F, Cl, Br, H, CN, $C_nF_{2n+1}$; n=1 to 12, $C_6F_5$.
$C_{10}F_aX_bL$ ($C_z$ is a naphthalene derivative) X=Cl, Br; $a+b=7$; L=F, Cl, Br, H, CN, $C_nF_{2n+1}$; n=1 to 12, $C_6F_5$.
$C_{12}F_aX_bL$ ($C_z$ is a biphenyl derivative) X=Cl, Br, $a+b=9$; L=F, Cl, Br, H, CN, $C_nF_{2n+1}$; n=1 to 12, $C_6F_5$.

The process of this invention does not require high pressure. Typical reaction pressures are about 0.01 to 100 atmospheres. The process can be operated in batch or continuous mode. Contact times are usually about 10 seconds or less for continuous runs and longer for batch runs. When operated continuously, with the desired product being continuously withdrawn, this equilibrium reaction offers a commercially attractive route to haloaromatic products.

Contemplated reaction temperatures are from 300° C. to 600° C. The preferred temperature range is 350° C. to 550° C. with the most preferred range being 400° C. to 500° C. Although the process can be run at temperatures less than 300° C., the reaction may be too slow to be practical. Although the process can be run at temperatures above 600° C., this process is characterized by the control over yield of desired product that is afforded by relatively mild reaction temperatures of no more than 600° C. At temperatures above 600° C., the disadvantages of carbon formation, reduced catalyst life and product decomposition become evident.

This control is strengthened by the selectivity afforded by the following class of catalysts. By selecting temperature and catalyst(s) within the scope of this disclosure, one skilled in the art will be able to maximize yield of the desired end product with an ease unavailable from previous high temperature or high pressure processes.

A preferred catalyst comprises $Cr_2O_3$ and up to 50% of one or more of the remaining numbers of group (ii). Another preferred catalyst comprises $Al_2O_3$ and up to 20% of one or more of FeO, NiO and CoO. The most preferred catalyst is $Cr_2O_3$ and the most preferred combinations are $Cr_2O_3/Al_2O_3$, $Cr_2O_3/NiO$ and $Al_2O_3/FeO$. $Al_2O_3$ is a preferred catalyst. $ZrO_2$, $TiO_2$ and MgO show some activity when used alone. Of course, $Cr_2O_3$ can be used in combination with catalyst group (iii) and $Al_2O_3$ can be used in combination with catalyst group (ii) to provide very good activity.

The amount of catalyst employed will depend on reactant flow rate. The reactive ratios of primary catalysts such as $Cr_2O_3$ and $Al_2O_3$ with the secondary Lewis Acid catalysts is not critical to operation of this invention. The disproportionation and/or transhalogenation reactions will proceed effectively with catalytic amounts of the primary catalyst(s) and with optional amounts of the secondary catalysts employed with the $Cr_2O_3$ or $Al_2O_3$ primary catalysts.

The following Examples illustrate the invention. All parts and percentages are by weight, and all degrees are Celsium unless otherwise noted. The Examples were run according to this procedure unless otherwise noted:

GENERAL PROCEDURE

A designated quantity of catalyst was charged to a 1-cm diameter x 10-cm long glass reactor [Vycor®] which was heated in a tube furnace. The feeds of haloaromatics were started together with a feed of nitrogen if one was used. The reactor effluent was condensed at $-78°$ and the product analyzed by GC, NMR or GC/MS. Analysis by GC was done on a DB 210 capillary column with a helium flow of 1.0 cc/sec. Temperatures for the GC analysis were 100° for 6 minutes followed by temperature programing at 20°/minute to 200°. The temperature was held at 200° until all products were eluted. Product compositions are expressed in area percent from a flame ionization detector.

EXAMPLES 1 TO 3

The reactor was charged with 5 grams of $Cr_2O_3$ and heated to 300° (Example 1). $C_6F_5Cl$ was fed to the reactor at 1 mL/hour along with nitrogen at 20 mL/minute. G.C. analysis of the effluent showed that some reaction had occurred. The reaction was repeated at 400° (Example 2) and 500° (Example 3). Analyses of the three runs by fluorine NMR gave the following composition. Example 1: $C_6F_5Cl$—6% conversion producing $C_6F_4Cl_2$—5%, $C_6F_3Cl_3$—1%; Example 2: $C_6F_5Cl$—12% conversion producing $C_6F_6$—2%, $C_6F_4Cl_2$—9%, and $C_6F_3Cl_3$—1%. Example 3: $C_6F_6$—8%, $C_6F_5Cl$—42%, m-$C_6F_4Cl_2$—36%, p-$C_6F_4Cl_2$—8%, o-$C_6F_2Cl_4$—6%.

EXAMPLES 4 TO 12

The reactor was charged with 10 grams of $Cr_2O_3$ and heated to the desired temperature. $C_6F_5Br$ was fed to the reactor at the indicated rate along with nitrogen at 5 mL/minute. The product was analyzed by GC. The results are given below.

| Example | Temp. | $C_6F_5Br$ mL/min | $C_6F_6$ | $C_6F_5Br$ | $C_6F_4Br_2$ | $C_6F_3Br_3$ |
|---|---|---|---|---|---|---|
| 4 | 350° | 1.0 | — | 93% | 0.38% | — |
| 5 | 400° | 0.5 | 1.4% | 89% | 5.2% | — |
| 6 | 420° | 0.4 | 1.3% | 87% | 7.4% | 0.4% |
| 7 | 440° | 0.3 | 1.9% | 78% | 11.5% | 1.0% |
| 8 | 460° | 0.3 | 4.7% | 70% | 16.1% | 1.5% |
| 9 | 480° | 0.3 | 5.6% | 69% | 19.8% | 2.3% |
| 10 | 500° | 0.3 | 8.7% | 65% | 21.1% | 2.5% |
| 11 | 520° | 0.3 | 8.5% | 65% | 23.8% | 2.5% |
| 12 | 540° | 0.3 | 7.9% | 63% | 28.1% | — |

EXAMPLE 13

The reactor was charged with 5 grams of $Cr_2O_3$ catalyst and heated to 500°. A mixture consisting of 0.3 g of $C_5Cl_5N$ [perchloropyridine] and 5 g of $C_5F_5N$ [perfluoropyridine] was fed to the reactor at 1 mL/hour along with nitrogen at 5 mL/minute. Analysis of the product by GC/MS gave the following results: $C_5F_5N$—87%, $C_5F_4ClN$—10.3%, $C_5F_3Cl_2N$—0.9%, $C_5F_2Cl_3N$—0.8%, $C_5FCl_4N$—0.2%, $C_5Cl_5N$—0.2%.

EXAMPLE 14

The reactor was charged with 5 grams of $Cr_2O_3$ catalyst and heated to 500°. A liquid feed of 1 mL/hour of $C_6F_5Br$ was fed to the reactor. A stream of 5 mL/minute of nitrogen was passed over a sample of perfluoronaphthalene kept in a 230° oil bath and conveyed to the reactor by a transfer line heated to 250°. Analysis of the product by GC/MS with an SE-30 capillary column gave the following results: $C_6F_5Br$—39%, $C_{10}F_8$—35%, $C_6F_4Br_2$—5.3%, $C_{10}F_7Br$—7.9%, $C_{10}F_6Br_2$—0.5%.

EXAMPLES 15 TO 17

The reactor was charged with 5 grams of $Cr_2O_3$ catalyst and heated to 400° (Example 15). A 3/1 molar mixture of $C_6F_5H/C_6F_5Br$ was fed to the reactor at 1 mL/hour along with nitrogen at 5 mL/minute. The reaction was repeated with the catalyst at 500° (Example 16) and 600° (Example 17). Analysis of the product from the 500° run by GC/MS showed the following distribution: $C_6F_5Br$—16%, $C_6F_4HBr$—5%, $C_6F_4Br_2$—6%, $C_6F_3Br_2H$—3%, $C_6F_3Br_3$—1%.

EXAMPLES 18 TO 22

The reactor was charged with 5 grams of $Cr_2O_3$ catalyst and heated to 400° (Example 18). A mixture containing 1 mL of $C_6F_5CN$ and 1 mL of $C_6F_5Br$ was fed to the reactor at 1 mL/hour along with nitrogen at 5 mL/minute. The reaction was repeated with the catalyst at 450°, 500°, 550° and 600° (Examples 19 to 22, respectively). Analysis of the product from the 600° run by GC/MS identified the following compounds: $C_6F_6$, $C_6F_5Br$, $C_6F_5CN$, $C_6F_4Br_2$, $C_6F_4BrCN$, $C_6F_3Br_2CN$.

EXAMPLES 23 TO 26

The reactor was charged with 5 grams of $Cr_2O_3$ catalyst and heated to 450°. A mixture containing 1 mL of $C_6F_5CF_3$ and 3 mL of $C_6F_5Br$ was fed to the reactor at 1 mL/hour along with nitrogen at 10 mL/minute. The reaction was repeated with the catalyst at 500°, 550° and 600°. Analysis of the product by GC gave the following results in addition to small amounts of $C_6F_2Br_4$ and $C_6F_3Br_3$:

| Ex. | Temp. | $C_6F_6$ | $C_6F_5CF_3$ | $C_6F_5Br$ | $C_6F_4CF_3Br$ | $C_6F_4Br_2$ |
|---|---|---|---|---|---|---|
| 23 | 450° | 12% | 32% | 50% | 0.8% | 5.4% |
| 24 | 500° | 15% | 22% | 34% | 4.7% | 11.6% |
| 25 | 550° | 19% | 22% | 33% | 7.8% | 12.7% |
| 26 | 600° | 16% | 19% | 29% | 8.5% | 14.4% |

EXAMPLES 27 TO 29

The reactor was charged with 5 grams of $Cr_2O_3$ catalyst and heated to a temperature of 400°. A mixture containing 1 gram of $[C_6F_5]_2$ and 3 mL of $C_6F_5Br$ was fed to the reactor at 1 mL/hour along with nitrogen at 10 mL/minute. The reaction was repeated with the catalyst at 500° and 600°. Analysis of the product by GC gave the following results.

| Ex. | Temp. | $C_6F_6$ | $C_6F_5Br$ | $C_6F_4Br_2$ | F—Biphenyl | $Br_xF$—Biphenyl |
|---|---|---|---|---|---|---|
| 27 | 400° | 21% | 64% | 5.0% | 1.9% | — |
| 28 | 500° | 22% | 50% | 8.2% | 4.5% | 4.9% |
| 29 | 600° | 20% | 44% | 15.9% | 7.6% | 6.8% |

EXAMPLES 30 AND 31

The reactor was charged with 5 grams of $Cr_2O_3$ catalyst and heated to 500° (Example 30). A mixture containing 2.5 grams of $C_6F_3Cl_3$ and 3 mL of $C_6F_5Br$ was fed to the reactor at 1 mL/hour along with nitrogen at 5 mL/minute. The reaction was repeated with the catalyst at 600° (Example 31). Analysis of the product from the 500° run by GC/MS gave the following results: $C_6F_6$—1.8%, $C_6F_5Cl$—2.1%, $C_6F_5Br$—11.4%, $C_6F_4Cl_2$—2.2%, $C_6F_3Cl_3$—14%, $C_6F_4Br_2$—6.7%.

Analysis of the product from the 600° run by GC/MS gave the following results:

$C_6F_6$—trace, $C_6F_5Cl$—2.8%, $C_6F_5Br$—12.4%,
$C_6F_4Cl_2$—10.5%, $C_6F_4BrCl$—12%,
$C_6F_3Cl_3$—19%, $C_6F_3BrCl_2$—12.3%,
$C_6F_3Br_2Cl$—11.6%, $C_6F_2BrCl_3$—8.8%,
$C_6F_2Br_2Cl_2$—4.6%, $C_6F_2Br_3Cl$—2.4%,
$C_6FBr_2Cl_3$—1.1%, $C_6FBr_3Cl_2$—0.3%,
$C_6Cl_4Br_2$—<1%, $C_6Cl_3Br_3$—<1%.

EXAMPLES 32 TO 35

The reactor was charged with 5 grams of $Cr_2O_3$ catalyst and heated to 400°. A mixture containing 2 grams of $C_6F_3Cl_3$ and 3 mL of $C_6F_6$ was fed to the reactor of 1 mL/hour along with nitrogen at 10 mL/minute. The reaction was repated with the catalyst at 500° and 600°. Analysis of the product by GC gave the following results.

| Ex. | Temp. | $C_6F_6$ | $C_6F_5Cl$ | $C_6F_4Cl_2$ | $C_6F_3Cl_3$ | $C_6F_2Cl_4$ | $C_6FCl_5$ |
|---|---|---|---|---|---|---|---|
| 32 | 400° | 54% | 1.3% | 1.0% | 32% | — | — |
| 33 | 500° | 48% | 9% | 3% | 27% | — | — |
| 34 | 600° | 39% | 22% | 14% | 19% | — | — |
| 35 | 600°* | nm | nm | 44% | 28% | 17% | 9% |

*Analysis by GC/MS; nm = not measured.

EXAMPLES 36 TO 64

The reactor was charged with 5 grams of the desired catalyst (Harshaw) and heated to 500° in air and purged with nitrogen. The catalyst was then adjusted to the desired temperature and $C_6F_5Br$ was fed to the reactor at a rate of 1 mL/hour along with nitrogen at 5 ml/minute. The product was collected and analyzed by GC. The results of these runs are given below.

| Ex. | Catalyst* | Temp | $C_6F_6$ | $C_6F_5Br$ | $C_6F_4Br_2$ |
|---|---|---|---|---|---|
| 36 | 1 | 500° | 7.8% | 88% | 4.4% |
| 37 | 2 | 500° | 6.8% | 74% | 14.8% |
| 38 | 3 | 400° | 4.2% | 91% | 5.2% |
| 39 | 3 | 500° | 0.8% | 90% | 7.6% |
| 40 | 4 | 450° | 7.3% | 83% | 6.3% |
| 41 | 4 | 550° | 7.4% | 78% | 3.6% |
| 42 | 5 | 400° | 0.3–0.5% | 65% | 22.5% |
| 43 | 6 | 500° | 3.4% | 89% | 4.9% |
| 44 | 6 | 600° | 4.5% | 66% | 19.5% |
| 45 | 7 | 500° | 1.2% | 94% | 3.6% |
| 46 | 7 | 600° | 1.1–3.3% | 64% | 20.6% |
| 47 | 8 | 600° | 2.4% | 91% | 2.0% |
| 48 | 9 | 500° | 2.9% | 86% | 10.8% |
| 49 | $Bi_2O_3/Al_2O_3$ | 600° | — | 71% | 21.1% |
| 50 | 10 | 500° | 9.3% | 10.8% | 3.1% |
| 51 | 11 | 500° | 16% | 76% | 3.1% |
| 52 | 9% $NiO/Cr_2O_3$ | 550° | 7.8% | 82% | 10% |
| 53 | $ZrO_2$ | 500° | 2.0% | 83% | 4.5% |
| 54 | 10% $P_2O_5/Cr_2O_3$ | 500° | 0.4% | 88% | 9.6% |
| 55 | 10% $B_2O_3/Cr_2O_3$ | 500° | 0.6% | 91% | 7.1% |
| 56 | $PbO/Al_2O_3$ | 500° | 22% | >6% | 0.3% |
| 57 | $PbO/Al_2O_3$ | 600° | 3.7% | 81% | 12.7% |
| 58 | $TiO_2$ | 500° | 8.2% | 91% | 4.4% |
| 59 | 10% $La_2O_3/Cr_2O$ | 500° | — | 95% | 3.4% |
| 60 | $MnO/Cr_2O_3$ | 500° | 3.3% | 90% | 3.1% |
| 61 | MgO | 500° | 9.7% | 82% | 7.6% |
| 62 | $CrCl_3/C$ | 500° | 25% | 16% | 1.2% |
| 63 | $Al_2O_3$ | 500° | 3.2% | 76% | 3.6% |

*1—Mn-0201 T ⅛" black tableted oxidation catalyst containing 19% manganese dioxide mounted on activated alumina.
2—Cr-0304 T ⅛" green tableted catalyst containing 33% $Cr_2O_3$ mounted on silicated alumina.
3—Fe-0301 T ⅛" dehydrogenation catalyst containing 20% $Fe_2O_3$ mounted on an activated alumina.
4—Ni-0707 T ⅛" tablet containing 14% nickel oxide on high activity alumina.
5—Pd-0509 T ⅛" tablet containing 0.3% palladium activated on a support.
6—Cr-0205 T 5/32" tablet containing 19% $Cr_2O_3$ mounted on activated alumina.
7—W-0101 T ⅛" yellow to white tablets containing 10% $WO_3$ mounted on activited alumina.
8—Co-0301 E 3/16 " black extrusions containing 10% cobalt oxide supported on alumina.
9—V-0701 T ⅛" orange tablets composed of 10% $V_2O_5$ mounted on a silica-containing alumina.
10—Cu-0905 P Catalyst containing 10% $CuCl_2$ mounted on activated alumina powder.
11—Al-1602 T ⅛" tablet-silicated high activity alumina catalyst containing 91% $Al_2O_3$ and 6% $SiO_2$ used as a catalyst support.

EXAMPLE 64

A stream of 5 mL/min of nitrogen was passed over a 5 g sample of 1,3,5-trichlorotrifluorobenzene kept at 200°. The vapor stream was passed through a catalyst bed of 5 g of $Cr_2O_3$ at 525° and the effluent collected at −78°. NMR analysis revealed that all possible isomers were present. Analysis by GC gave the following results: $C_6F_5Cl$—3.2%; $C_6F_4Cl_2$—18%; $C_6F_3Cl_3$—62%; $C_6F_2Cl_4$—16%; $C_6FCl_5$—2%.

EXAMPLE 65

A mixture of 5 ml/min of nitrogen and 1 mL/hr of $C_6F_5I$ was passed over 5 g of a catalyst comprising 80% CuO and 17% $Cr_2O_3$ at 300° which had been previously heated to 400° in a stream of 5 mL/min hexafluoropropene. The purple product which was collected at −78° contained all three isomers of $C_6F_4I_2$ (4%) and $C_6F_6$ (4%) in addition to 23% $C_6F_5H$ and 67% $C_6F_5I$.

EXAMPLES 66 AND 67

A mixture of 5 g of mixed isomers of $C_6F_4Cl_2$ and 4.4 g of mixed isomers of $C_6F_2Cl_4$ was fed to 5 g of $Cr_2O_3$ at 1.0 ml/hr along with a carrier stream of 5 mL/min of nitrogen. A GC of the starting material showed $C_6F_4Cl_2$, 45%; $C_6F_3Cl_3$, 0.8%; and $C_6F_2Cl_4$, 50%. GC analysis of the product gave the following results.

| Ex. | Temp. | $C_6F_5Cl$ | $C_6F_4Cl_2$ | $C_6F_3Cl_3$ | $C_6F_2Cl_4$ | $C_6FCl_5$ |
|-----|-------|------------|--------------|--------------|--------------|------------|
| 66  | 500   | 2%         | 38%          | 16%          | 23%          | 5%         |
| 67  | 525   | 2%         | 21%          | 29%          | 31%          | 12%        |

EXAMPLE 68

A mixture of 1 g of $C_6FCl_5$ and 0.2 g of $Cr_2O_3$ was heated at reflux in a glass round bottom flask with an air condenser. The time of reaction was uncertain because the solid product periodically sublimed to the colder part of the system and had to be melted to again contact the catalyst. A GC analysis of the product showed $C_6F_2Cl_4$, 5%; $C_6FCl_5$ 83%; and $C_6Cl_6$, 10%.

COMPARATIVE EXAMPLES A AND B

The reactor was charged with 5 grams of aluminum fluoride (Harshaw Al-1101T; ¼" tablets containing 85% or more aluminum fluoride] and heated to 400° (Example A); another run was heated to 500° (Example B). $C_6F_5Cl$ was fed to the reactor at a rate of 1 mL/hour along with nitrogen at 5 mL/minute. G.C. analysis of both runs showed that no reaction had occurred.

I claim:

1. A catalyst method for rearranging haloaromatic compounds according to the equation $$C_zF_aX_bN_eL_1 + C_zF_cX_dN_eL_2 \rightarrow C_zF_{a+1}X_{b-1}N_eL_1 + C_zF_{c-1}X_{d+1}N_eL_2$$

wherein:
when $C_z$ is benzene, $a+b=5$; $e=0$; $c+d=5$; $z=6$;
when $C_z$ is a pyridine, $a+b=4$; $e=1$; $c+d=4$; $z=5$;
when $C_z$ is a naphthalene, $a+b=7$; $e=0$; $c+d=7$; $z=10$; and
when $C_z$ is a biphenyl, $a+b=9$; $e=0$; $c+d=9$; $z=12$;
$L_1$ and $L_2$, alike or different, are selected from F, Cl, Br, H, CN, $C_nF_{2n+1}$, and $C_6F_5$;
X is Cl, Br, or I when $C_z$ is a benzene; and
n is 1 to 12;
at a temperature of about 300° to 600° C., in the presence of a catalyst selected from the group consisting of:
(i) $Cr_2O_3$ and $Al_2O_3$ alone or together;
(ii) $Cr_2O_3$ and one or more members from the group MnO, $MnO_2$, $P_2O_5$, $B_2O_3$, $La_2O_3$, ZnO, $Fe_2O_3$, NiO, Pd, $WO_3$, CoO, $V_2O_5$, $CuCl_2$, CuO, PbO, $Bi_2O_3$, FeO, NiO, CoO, $ZrO_2$, $TiO_2$, MgO and $CrCl_3$; and
(iii) $Al_2O_3$ and one or more members from the group MnO, $MnO_2$, $P_2O_5$, $B_2O_3$, $La_2O_3$, ZnO, $Fe_2O_3$, NiO, Pd, $WO_3$, CoO, $V_2O_5$, $CuCl_2$, CuO, PbO, $Bi_2O_3$, FeO, NiO, CoO, $ZrO_2$, $TiO_2$, MgO and $CrCl_3$.

2. A method according to claim 1 wherein $a+b=5$, $e=0$, $c+d=5$, $z=6$.
3. A method according to claim 1 wherein $a+b=4$, $e=1$, $c+d=4$, $z=5$.
4. A method according to claim 1 wherein $a+b=7$, $e=0$, $c+d=7$, $z=10$.
5. A method according to claim 1 wherein $a+b=9$, $e=0$, $c+d=9$, $z=12$.
6. A method according to claim 2 wherein X is Cl.
7. A method according to claim 6 wherein $b=3$.
8. A method according to claim 7 wherein $d=4$.
9. A method according to claim 6 wherein $b=5$.
10. A method according to claim 2 wherein X is Br.
11. A method according to claim 2 wherein X is I.
12. A method according to claim 3 wherein X is Cl, Br.
13. A method according to claim 1 wherein the catalyst comprises $Cr_2O_3$.
14. A method according to claim 1 wherein the catalyst comprises $Al_2O_3$.
15. A method according to claim 1 wherein the catalyst comprises $Cr_2O_3$ and $Al_2O_3$.
16. A method according to claim 1 wherein the catalyst comprises catalyst group (ii).
17. A method according to claim 1 wherein the catalyst comprises catalyst group (iii).
18. A method according to claim 2 wherein the catalyst comprises $Cr_2O_3$.
19. A method according to claim 2 wherein the catalyst comprises $Al_2O_3$.
20. A method according to claim 2 wherein the catalyst comprises $Cr_2O_3$ and $Al_2O_3$.
21. A method according to claim 2 wherein the catalyst comprises catalyst group (ii).
22. A method according to claim 2 wherein the catalyst comprises catalyst group (iii).
23. A method according to claim 3 wherein the catalyst comprises $Cr_2O_3$.
24. A method according to claim 3 wherein the catalyst comprises $Al_2O_3$.
25. A method according to claim 3 wherein the catalyst comprises $Cr_2O_3$ and $Al_2O_3$.
26. A method according to claim 3 wherein the catalyst comprises catalyst group (ii).
27. A method according to claim 3 wherein the catalyst comprises catalyst group (iii).
28. A method according to claim 16 wherein the catalyst comprises $Cr_2O_3$ and up to 50% of one or more of the remaining members of group (ii).
29. A method according to claim 21 wherein the catalyst comprises $Cr_2O_3$ and up to 50% of one or more of the remaining members of group (ii).
30. A method according to claim 26 wherein the catalyst comprises $Cr_2O_3$ and up to 50% of one or more of the remaining members of group (ii).
31. A method according to claim 17 wherein the catalyst comprises $Al_2O_3$ and up to 20% of one or more of FeO, NiO and CoO.
32. A method according to claim 22 wherein the catalyst comprises $Al_2O_3$ and up to 20% of one or more of FeO, NiO and CoO.
33. A method according to claim 27 wherein the catalyst comprises $Al_2O_3$ and up to 20% of one or more of FeO, NiO and CoO.

* * * * *